US007311906B2

(12) United States Patent
Lallatin et al.

(10) Patent No.: US 7,311,906 B2
(45) Date of Patent: Dec. 25, 2007

(54) ANTI-VIRAL ACTIVITY OF AN ANTI-THYMIDINE KINASE MONOCLONAL ANTIBODY

(75) Inventors: Nathaniel Lallatin, Meridian, ID (US); Kim L. O'Neill, Provo, UT (US)

(73) Assignee: Brigham Young University, Provo, UT (US)

( * ) Notice: Subject to any disclaimer, the term of this patent is extended or adjusted under 35 U.S.C. 154(b) by 127 days.

(21) Appl. No.: 11/116,937

(22) Filed: Apr. 28, 2005

(65) Prior Publication Data

US 2006/0024311 A1 Feb. 2, 2006

Related U.S. Application Data

(60) Provisional application No. 60/567,344, filed on Apr. 30, 2004.

(51) Int. Cl.
*A61K 39/00* (2006.01)
*A01N 1/02* (2006.01)
*G01N 33/53* (2006.01)

(52) U.S. Cl. .............................. 424/93.1; 530/388.26; 530/388.3; 424/184.1; 435/320.1; 435/2; 435/7

(58) Field of Classification Search ............. 424/184.1; 435/302.1
See application file for complete search history.

(56) References Cited

U.S. PATENT DOCUMENTS

| | | | |
|---|---|---|---|
| 4,317,877 A | 3/1982 | Balis et al. | |
| 4,474,893 A | 10/1984 | Reading | |
| 4,722,899 A | 2/1988 | Hamaoka et al. | |
| 4,816,567 A | 3/1989 | Cabilly et al. | |
| 5,476,996 A | 12/1995 | Wilson et al. | |
| 5,514,548 A | 5/1996 | Krebber et al. | |
| 5,698,409 A | 12/1997 | O'neill | |
| 5,869,045 A | 2/1999 | Hellstrom et al. | |
| 6,083,707 A | 7/2000 | Eriksson et al. | |
| 6,331,415 B1 | 12/2001 | Cabilly et al. | |
| 6,372,217 B1 | 4/2002 | Uckun | |
| 2006/0039914 A1 | 2/2006 | Lallatin et al. | |

FOREIGN PATENT DOCUMENTS

| | | |
|---|---|---|
| EP | 0042482 | 12/1981 |
| EP | 0255431 | 10/1991 |
| EP | 0454478 | 10/1991 |
| WO | 9306213 | 4/1993 |
| WO | 9708320 | 3/1997 |

OTHER PUBLICATIONS

Groschel et al. Infection 2000, vol. 28, No. 4, pp. 209-213.*
U.S. Appl. No. 60/567,344 filed Apr. 30, 2004, Lallatin.
Balzarini et al. (1982) "Role of Thymidine Kinase in the Inhibitory Activity of 5-Substituted-2'Deoxyuridines on the Growth of Human and Murine Tumor Cell Lines," Biochem. Pharmacol. 31(6):1089-1095.
Baron et al. (1990) "A Rapid Two-Step Purification of Rat Liver Fetal Thymidine Kinase," Preparative Biochem. 20 (3-4):241-256.
Boivin et al. (2002) "Intranasal Herpes Simplex Virus Type 2 Inoculation Causes a Profound Thymidine Kinase Dependent Cerebral Inflammatory Response in the Mouse Hindbrain," Eur. J. Neurosci. 16(1):29-43.
Bradshaw, H.D. Jr. (1983) "Molecular Cloning and Cell-Specific Regulation of a Functional Human Thymidine Kinase Gene," Proc. Natl. Acad. Sci. USA 80:5588-5591.
Bronzert et al. (1981) "Purification and Properties of the Estrogen-Responsive Cytoplasmic Thymidine Kinase from Human Breast Cancer," Cancer Res. 41:604-610.
Daugherty et al. (1991) "Polymerase Chain Reaction Facilitates the Cloning, CDR-Grafting, and Rapid Expression of a Murine Monoclonal Antibody Directed Against the CD18 Component of Leukocyte Integrins," Nuc. Acids Res. 19 (9):2471-2476.
Ellims et al. (1982) "Human Thymidine Kinase: Purification and Some Properties of the TK1 Isoenzyme from Placenta," Mol. Cell. Biochem. 45:113-116.
Flemington (1987) "Sequence, Structure and Promoter Characterization of the Human Thymidine Gene," Gene 52:267-277.
Gan et al. (1983) "Human Thymidine Kinase," J. Biol. Chem. 258:7000-7004.
Goding et al. (1980) "Antibody Production by Hybridomas," J. Immunol. Methods 39:285-308.
Gronowitz et al. (1984) "Application of an In Vitro Assay for Serum Thymidine Kinase: Results on Viral Disease and Malignancies in Humans," Int. J. Cancer 33:5-12.
Habteyesus et al. (1991) "Deoxynucleside Phosphorylating Enzymes in Monkey and Human Tissues Show Great Similarities, While Mouse Deoxycytidine Kinase has a Different Substrate Specificity," Biochem. Pharmacol. 42(9):P1829-P1836.
Hannigan et al. (1993) "Thymidine Kinase: The Enzymes and Their Clinical Usefulness," Cancer Biother. 8(3):187-197.
Hengstschlager et al. (1994) "Different Regulation of Thymidine Kinase During the Cell Cycle of Normal Versus DNA Tumor Virus-Transformed Cells," J. Biol. Chem. 269:13836-13842.
Hengstschlager et al. (1994) "A Common Regulation of Genes Encoding Enzymes of the Deoxynucleotide Metabolism is Lost After Neoplastic Transformation," Cell Growth Differ. 5(12):1389-1394.
Hengstschlager et al. (1993) "Cytofluorometric Assay for the Determination of Thymidine Uptake and Phosphorylation in Living Cells," Cytometry 14:39-445.
Jansson et al. (1992) "Mammalian Thymidine Kinase 2, Direct Photoaffinity Labeling with [32P]dTTP of the Enzyme from Spleen, Liver, Heart and Brain," Eur. J. Biochem. 206(2):485-490.
Kohler et al. (1976) "Derivation of Specific Antibody-Producing Tissue Culture and Tumor Lines by Cell Fusion," J. Immunol. 6:511-519.

(Continued)

*Primary Examiner*—Bruce R. Campbell
*Assistant Examiner*—Bao Qun Li
(74) *Attorney, Agent, or Firm*—Greenlee, Winner and Sullivan, P.C.

(57) ABSTRACT

Monoclonal antibodies to thymidine kinase 1 are disclosed which are useful in methods of detecting, diagnosing, and treating viral infection.

11 Claims, 2 Drawing Sheets

OTHER PUBLICATIONS

Lau et al. (1994) "Direct Isolation of the Functional Human Thymidine Kinase Gene W/A Cosmid Shuttle Vector," Proc. Natl. Acad. Sci. USA 81:414-418.

May et al. (1991) "Intracellular Routing Rather than Cross-Linking or Rate of Internalization Determines the Potency of Immunotoxins Directed Against Different Epitopes of sigD on Murine B Cells," Cell Immunol. 135:490-500.

McKenna et al. (1988) "Thymidine Kinase Activities in Mononuclear Leucocytes and Serum from Breast Cancer Patients," Br. J. Cancer 57:619-622.

Munch-Peterson et al. (1990) "Thymidine Kinase in Human Leukemia—Expression of Three Isoenzyme Variants in Six Patients with Chronic Myelocytic Leukemia," Leuk. Res. 14:39-45.

Munch-Peterson et al. (1991) "Diverging Substrate Specificity of Pure Human Thymidine Kinases 1 and 2 Against antiviral Dideoxynucleosides," J. Biol. Chem. 266:9032-9038.

Munch Peterson et al. (1993) "Reversible ATP-Dependent Transition Between Two Forms of Human Cytosolic Thymidine Kinase With Different Enzymatic Properties," J. Biol. Chem. 268(21):15621-15625.

Oldham et al. (1993) "Whats the Score," Cancer Biother. 8(3):187-188.

O'Neill et al. (1992) "Can Thymidine Kinase Levels in Breast Tumors Predict Disease Recurrence," J. Nat. Cancer Inst. 84(23):1825-1828.

O'Neill et al. (1987) "Elevated Serum and Mononuclear Leukocyte Thymidine Kinase Activities in Patients with Cancer," Irish Med. J. 80(9):264-265.

Seaver et al. (1994) "Monoclonal Antibodies in Industry: More Difficult Than Originally Thought," Genetic Eng. News pp. 10,21.

Sherley et al. (1988) "Human Cytosolic Thymidine Kinase," J. Biol. Chem. 263:375-391.

Tamiya et al. (1989) "Co-Purification of Thymidylate Kinase and Cytosolic Thymidine Kinase from Human Term Placenta by Affinity Chromatography," Biochem. Biophys. Acta 995:28-35.

Topolcan et al. (2005) "Changes of Thymidine Kinase (TK) During Adjuvant and Palliative Chemotherapy," Anticancer Res. 25:1831-1834.

Willingham et al. (1987) "Pseudomonas Exotoxin Coupled to a Monoclonal Antibody Against Ovarian Cancer Inhibits the Growth of Human Ovarian Cancer Cells in a Mouse Model," Proc.Natl. Acad. Sci. USA 84:2474-2478.

* cited by examiner

Western Blot

(a)

(b)

ANTI-VIRAL ACTIVITY OF AN ANTI-THYMIDINE KINASE MONOCLONAL ANTIBODY

RELATED APPLICATIONS

This application claims priority to U.S. Provisional application No. 60/567,344, filed Apr. 30, 2004, which is incorporated herein by reference.

BACKGROUND OF THE INVENTION

1. Field of the Invention

Embodiments of the invention relate to treatment of a viral infection with a monoclonal antibody to thymidine kinase.

2. Description of the Related Art

Thymidine kinase (ATP:thymidine-5' phosphotransferase; EC 2.7.1.21 in the International Union of Biochemistry classification system) is an enzyme that phosphorylates thymidine to thymidine monophosphate (TMP). The commonly used abbreviation of TK will be used herein to denote thymidine kinase in a general sense, where different TK isozymes are not specified particularly.

Thymidine kinase protein has been isolated from many different sources and purified to varying degrees. A variety of different molecular weight thymidine kinases have been reported from human samples, depending on the particular cell and the method of isolation and analysis. In general, the findings suggest that thymidine kinase exists in at least one monomeric form and a variety of multimeric forms.

In humans, it is also known that there are at least two major isozymes (similar but distinct forms) of thymidine kinase, referred to herein as TK1 and TK2. These isozymes are produced from different genes, are found in different cellular compartments, and differ in their levels and timing of expression during the cell cycle and according to the cell differentiation state. In humans, the TK1 gene is on chromosome 17 in band q21-22 (Elsevier 1974) while the TK2 gene is on chromosome 16 (Willecke et al. (1977) Somatic Cell Genet. 3:237). A gene for TK1 has been cloned and sequenced (Lin (1984) Proc. Nat'l Acad. Sci. 81:414-418; Flemington (1987) Gene 52:267-277).

There are extensive inconsistent reports in the prior art on the properties of mammalian TK1, with diverging results and observations as to the electrophoretic behavior and kinetic properties. Native molecular weights between 45,000 and 200,000 daltons have been reported for the native human TK1 from, for example, leukemic cells (96 kD, Sherley et al. (1988) J. Biol. Chem 263:375-391; 150-200 kD, Munch-Petersen et al., (1990) Leuk. Res. 14:39-45), human placenta (45 kD, Ellims et al. (1982) Mol. Cell. Biochem. 45:113-116); 92 kD, Gan et al. (1983) J. Biol. Chem. 258:7000-7004; 70 kD, Tamiya et al. (1989) Biochim. Biophys. Acta 995:28-35), lymphocytes (110 kD, Munch-Petersen et al. (1991) J. Biol. Chem. 266:9032-9038), and human breast cancer (177 kD, Bronzert et al. (1981) Cancer Res. 41:604-610).

It has been reported that in the presence of ATP, native TK1 shifts to a form of TK1 having a higher molecular weight, for example, human placental TK1 of 50 kD shifts to 70 kD in the presence of ATP (Tamiya et al. (1989), supra) and human lymphocytic TK1 of 55 kD shifts in the presence of ATP to a form having a molecular weight of 110 kD (Munch-Petersen et al. (1991) supra).

Not only are widely divergent values reported for the molecular weight of the native TK1, different views exist in the prior art for the monomeric subunit of TK1. Molecular weights of 44 and 22-24 kD have been reported for the TK1 monomer. Further, reports vary as to whether the monomeric subunit is associated with TK1 enzymatic activity. For example, TK1 enzyme activity has been reported to be associated with the monomeric subunit of approximately 24 kD for the HeLa cells (Sherley et al. (1988) supra), rat liver (Baron et al. (1990) Preparative Biochemistry 20:241-256), and human lymphocytes (Munch-Petersen (1991) supra), but enzyme activity was not found associated with the monomeric subunit in the presence or absence of ATP for human placenta TK1 (Tamiya et al. (1989) supra).

Balis et al. (U.S. Pat. No. 4,317,877, Mar. 2, 1982) disclosed immunesera to a small subunit component of (a) TK from normal colonic mucosa and (b) TK from term human placenta. Although both small subunit components were electrophoretically similar, they were not antigenically identical as indicated by differences in precipitin patterns. Moreover, it was stated that "The lack of complete neutralization by these antisera of their respective homologous enzymes is not unexpected since only the small molecular weight component is used as antigen." The teaching in the Balis et al. patent, supra, is that an antiserum to a subunit component of TK1 does not completely react with nor neutralize the active multimeric form of the TK1. Also, the Balis antibody did not react with leukemic leukocytes or with normal or mitogen-stimulated peripheral lymphocytes, even though these are known to have elevated TK levels (Balis et al., col. 2, lines 21-23).

Another European Patent publication, No. 0 255 431 by Jouan published Oct. 23, 1991, discloses purification of "TK-F" (fetal TK or TK1) from human placental material for purposes including the use of the pure TK-F to produce anti-TK-F antibodies. Jouan teaches the purification of TK-F using prior art technology which has been shown in various reports to result in the purification of a TK1 so labile that yields of purified TK are insufficient for further manipulation, e.g., for biochemical characterization, monoclonal antibody preparation, screening, etc. Jouan suggests the use of art-known methods to prepare monoclonal antibody using his purified TK-F, however, the patent does not teach how to overcome the problem of extreme lability associated with a purified TK1 obtained using prior art methodologies, a problem noted in many prior art references.

U.S. Pat. No. 5,698,409, issued Dec. 16, 1997, which is incorporated herein by reference, describes a purified mammalian thymidine kinase 1 (TK1) from Raji cells and a TK1 monoclonal antibody. Raji cells are an immortalized human lymphoma cell line, available from ATCC as cell line #CCL-86. U.S. Pat. No. 5,698,409 also describes a monoclonal antibody to TK1 which not only binds to TK1 but also inhibits TK1 activity. Specific anti-TK1 antibody monoclonal producing hybridomas are available as ATCC HB 11432, HB 11433, HB 11434, and PTA-6704.

TK-1 is a cellular enzyme which is involved in a "salvage pathway" of DNA synthesis. In normal growing cells thymidine kinase 1 mRNA rises near the G1-S boundary, peaks in early S phase, and returns in G2 to approximately the level of early G1. It is activated in the G1/S phase of the cell cycle, and its activity has been shown to correlate with the proliferative activity of tumor cells. Proliferating cells appear to have lost the strict regulation of TK1 that is observed in normal cells. TK activity is a major biochemical marker of cell proliferation and several studies show that TK levels are elevated in malignancies.

In DNA tumor virus-transformed cells, the level of TK mRNA remains relatively constant throughout all phases of the cell cycle. Data suggest that DNA tumor viruses suppress a transcriptional down-regulation common to enzymes responsible for the DNA precursor pathway. In virally transformed cells lines both TK1 mRNA levels and TK1activity remain elevated throughout the cell cycle (Different regulation of thymidine kinase during the cell cycle of normal versus DNA tumor virus-transformed cells. Hengstschlager, M., Knofler, m., Mullner, E. W., Ogris, E., Wintersberger, E., Wawra, E. J. Biol. Chem., 269: 13836-13842, 1994). The step catalysed by thymidine kinase 1 is the bottle neck of the S-phase gene pathway and is therefore rate limiting. Even slow-growing cancers or latent viral infections constitutively express TK1 on the cell surface making them susceptible to ADCC and CDC (A common regulation of genes encoding enzymes of the deoxynucleotide metabolism is lost after neoplastic transformation. Hengstschlager M, Mudrak I, Wintersberger E, Wawra E. Cell Growth Differ. 1994 December;5(12):1389-94. Vienna Biocenter, University of Vienna, Austria).

Relationship to TK1 and HIV, CMV, HCV, Papilloma, Polyoma, Adenovirus, etc . . .

T cell synthesis of dNTP by Thymidine Kinase is required by HIV for reverse transcription by reverse transcriptase and integration of the viral genome into the host DNA. The site of viral genome integration of TK1 in SHIV infection results in the over-expression of thymidine kinase mRNA, which is abolished by highly active antiretroviral therapy (HAART) The expression of P-glycoprotein and cellular kinases is modulated at the transcriptional level by infection and highly active antiretroviral therapy in a primate model of AIDS (Jorajuria S, Clayette P, Dereuddre-Bosquet N, Benlhassan-Chahour K, Thiebot H, Vaslin B, Le Grand R, Dormont D. AIDS Res Hum Retroviruses. 2003 April;19 (4):307-11. CEA, Service de Neurovirologie, DRM/DSV, CRSSA, EPHE, IPSC, 92265 Fontenay-aux-Roses, France).

Likewise Cytomegaloviruses (CMVs) do not encode many of the biosynthetic enzymes for DNA precursor synthesis. The virus requires a mechanism to overcome cellular quiescence. HCMV infection induces the progression of quiescent cells toward the G1_S transition point and activates the TK1 gene required for DNA replication. When HFF cells were infected with HCMV Towne strain, and cytoplasmic RNAs were harvested at 6 and 24 h after infection, there was an increase in steady-state RNA levels of many genes for cell cycle progression to the G1_S transition point (Effect of the human cytomegalovirus IE86 protein on expression of E2F-responsive genes: A DNA microarray analysis. Yoon-Jae Song and Mark F. Stinski. PNAS Mar. 5, 2002, vol. 99, no. 5). All of these studies indicate that levels of TK1 are elevated during periods of cell proliferation such as viral infection.

Likewise, in cells transformed with polyoma virus, papilloma virus, adenovirus, or SV40, TK activity as well as TK mRNA was consistently higher in all phases of the cell cycle, and TK mRNA never displayed significant cell cycle-dependent changes. Furthermore, it is possible to up-regulate TK mRNA and enzyme activity throughout the normal cell cycle simply by expressing the polyoma large T antigen in a cell line carrying the information for this protein in inducible form. This work presents evidence that DNA tumor viruses have a mechanism to keep TK expression high during the cell cycle ("Different regulation of thymidine kinase during the cell cycle of normal versus DNA tumor virus-transformed cells. Hengstschlager, M., Knofler, m., Mullner, E. W., Ogris, E., Wintersberger, E., Wawra, E. J. Biol. Chem., 269: 13836-13842, 1994)."

The use of MAb to specifically target viral-infected cells is an approach which can leave normal or uninfected tissue or cells unharmed. MAb's may be used to construct therapeutic reagents with selectivity for certain populations of cells. Optionally, MAbs or other cell targeting proteins are linked to bioactive moieties to form biotherapeutic agents referred to as immunoconjugates, immunotoxins or fusion proteins, which can combine the selectivity of the targeting moiety with the potency of the bioactive moiety. Embodiments of the invention are directed to the use of anti-TK1 antibody to inhibit cell proliferation in cells that synthesize and express TK1 such as virally-infected cells as well as the use of anti-TK1 antibodies in diagnosis of viral infection.

SUMMARY OF THE INVENTION

In some embodiments, the invention is directed to a method for treating a viral infection in a mammal, which includes the steps of administering to the mammal, an amount of a pharmaceutical composition which includes an anti-TK1 antibody or fragment thereof, sufficient to inhibit viral replication or reduce viral burden in the mammal. Preferably, the anti-TK1 antibody is a monoclonal antibody. More preferably, the anti-TK1monoclonal antibody is 5G11.

In preferred embodiments, the anti-TK1 antibody is a humanized or fully human monoclonal antibody.

In some embodiments, the pharmaceutical composition further also includes a second antiviral agent. Preferably, the second antiviral agent is a nucleoside analog, non-nucleoside analog, protease inhibitor, or entry inhibitor.

In some embodiments, the anti-TK1 antibody is conjugated to a cytotoxic agent. Preferably, the cytotoxic agent is pokeweed antiviral protein (PAP), ricin, abrin, gelonin, saporin, or alpha-sarcin.

In some embodiments, prior to administering the pharmaceutical composition, the mammal is treated with sufficient radiation to up-regulate TK1 expression.

In some preferred embodiments, the pharmaceutical composition also includes a pharmaceutically acceptable liquid carrier adapted for parenteral administration. Preferably, the liquid carrier includes isotonic saline.

In some embodiments, the invention is directed to a method for diagnosing a viral infection in a mammal, which includes the steps of obtaining a sample from the mammal, incubating the sample with an anti-TK1 antibody or fragment thereof, detecting an amount of antibody-TK1 complex, quantifying the concentration of TK1 in the sample by comparing the detected amount of antibody-TK1 complex with a standard curve generated using known amounts of TK1, and diagnosing the presence of a viral infection in the mammal based on the concentration of TK1 in the sample.

Further aspects, features and advantages of this invention will become apparent from the detailed description of the preferred embodiments which follow.

BRIEF DESCRIPTION OF THE DRAWINGS

These and other features of this invention will now be described with reference to the drawings of preferred embodiments which are intended to illustrate and not to limit the invention.

DETAILED DESCRIPTION OF THE PREFERRED EMBODIMENT

Figure 1:
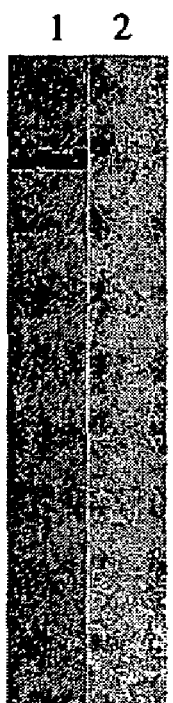
FIG. 1 shows Western blot assay showing TK1 specificity of clone 14F2. Samples were separated using a native or a partial denature 12% polyacrylamide gel. Polypeptides were then transferred onto a nitrocellulose filter and probed with MAb from clone 14F2. A conjugate antibody solution containing goat anti-mouse IgG (H1L chains) horseradish peroxidase was used to visualize MAb binding. (a) Lane 1, purified TK1, native sample, Ponceau S staining: Lane 2, purified TK1 native sample, Western blot. (b) Lane 1, purified TK1, partial denature sample, Ponceau S staining; Lane 2, Purified TK1, partial denature sample, Western blot; Lane 3; Raji cell extract, partial denature sample, Western blot; Lane 4, Hela cell extract, partial denature sample, Western blot.
Figure 1:
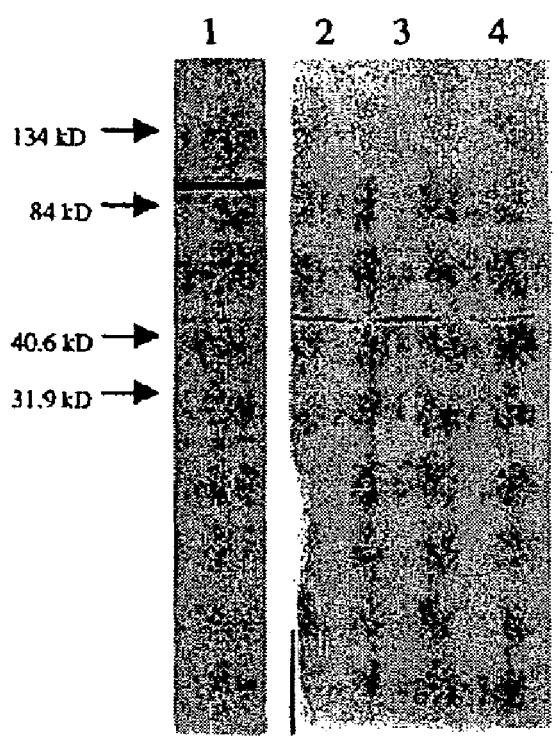

While the described embodiment represents the preferred embodiment of the present invention, it is to be understood that modifications will occur to those skilled in the art without departing from the spirit of the invention. The scope of the invention is therefore to be determined solely by the appended claims.

The following definitions are provided in order to provide clarity as to the intent or scope of their usage in the specification and claims.

The term "mammalian thymidine kinase 1 or TK1" as used herein refers to an enzymatically active TK1. In preferred modes, the TK1 is isolated and purified from a mammal, including, but not limited to, a mammalian body organ, tissue, cell, fluid and the like, in either normal or diseased condition, and presented as a fresh or preserved specimen, a cell tissue culture, a cell line, a hybridoma, etc. Alternatively, the mammalian TK1 may be produced in host cells, preferably mammalian host cells, which have been engineered to contain a polynucleotide sequence that encodes enzymatically active TK1. In one preferred embodiment, the polynucleotide encoding the enzymatically active TK1 is operably linked to an inducible promoter. Preferably, the purified TK1 of the invention, whether isolated from tissues or cells, or produced by recombinant DNA methods, provides a yield of purified TK1 sufficient for the preparation of antibodies to TK1.

The "term mammalian" as used herein refers to a human or other animal classified as a mammal.

The term "body fluid" as used herein refers to any fluid obtained from a mammal, for example, blood, serum, urine, spinal fluid, tears, etc.

The term "body tissue" as used herein refers to any normal or diseased tissue obtained from a mammal, for example, organ tissue, biopsy tissue, tumors, etc. A body tissue may be presented as a fresh or preserved (e.g., frozen) sample, a histological slide preparation, etc.

The terms "antibody" or "immunoglobulin" are used generally to include polyclonal and monoclonal antibodies, and fragments thereof which exhibit the desired binding specificity and affinity, regardless of the source or immunoglobulin type (i.e., IgG, IgE, IgM, etc.). The term "antibody to TK1", "TK1 antibody" or "anti-TK1 antibody" as used herein refers to an antibody or fragment thereof that binds to TK1. The term "monoclonal antibody" is used in accordance with its ordinary meaning to denote a homogenous immunoglobulin resulting from the proliferation of a single clone of cells (e.g., hybridoma cells, eukaryotic host cells transfected with DNA encoding the homogenous immunoglobulin, prokaryotic host cells transformed with DNA encoding the homogenous immunoglobulin, etc.), and which is generally characterized by heavy chains of a single class and subclass, and light chains of a single type. It is contemplated that in some applications a polyclonal antibody to a purified TK1 of the instant invention can be utilized in place of an anti-TK1 monoclonal antibody of the invention. Note that not all TK1 antibodies inhibit the TK1 enzymatic activity because not all epitopes are at the catalytic site. Some antibodies were obtained that bound to TK1 but did not inhibit the TK1 enzymatic activity.

The term "therapeutic application" as used herein refers to any use of TK1, anti-TK1 monoclonal antibodies, or anti-TK1 polyclonal antibodies to target diseased tissues, wherein said diseased tissues are targeted, visualized, decreased or eliminated. It is contemplated that the therapeutic applications of this invention may be used in conjunction with or in isolation from other now known or yet to be discovered therapeutic applications.

The term "biotherapeutic agent" is used in its ordinary sense and to include the use of a MAb, pharmaceutical, protein or peptide, nucleic acid, etc. to treat or prevent disease or other abnormality in a mammal such as a human.

The term "complement mediated lysis" as used herein refers to a system of serum proteins activated by antibody-antigen complexes or by microorganisms, which helps eliminate selected microorganisms or cells by directly causing their lysis or by promoting their phagocytosis.

The terms "humanized immunoglobulin" or "humanized antibody" are used in their ordinary meanings and include any immunoglobulin or antibody or fragment thereof, produced at least partly in a non-human mammal, wherein at least one portion is of human origin.

The following described embodiments for the production of anti-TK1 are to be considered in all respects only as illustrative and not restrictive. In preferred embodiments, the current invention contemplates the production of various antibodies comprising antibodies specific to active TK1, inactive TK1, multimeric TK1, and monomeric TK1. Additionally, in preferred embodiments, the current invention contemplates the production of various anti-TK1 antibodies, which are specific to various TK1 epitopes. Consequently, the scope of this disclosure should not be read as to limit the invention to a finite number of antibodies or to a finite number of epitopes on TK1.

The present inventors have found that TK1 is found on the surface of proliferating cells and virally-infected cells, but not normal cells. TK1 expression is increased 6-30 times during viral transformation or infection of mammalian cells. This observation is utilized in methods disclosed herein for treating virally-infected cells with an antibody to thymidine kinase. Methods based upon the observed mechanism pertaining to the treatment of proliferating (e.g., cancer) cells are disclosed in co-pending U.S. provisional application No. 60/1549147, which is incorporated herein by reference.

It has been demonstrated that TK1 mRNA and protein are up-regulated and constitutively expressed in virally-infected and virally-transformed cells (HSV-1, HSV-2, varicella-zoster virus (VZV), vaccinia virus, vesicular stomatitis, cytomegalovirus (CMV), and human immunodeficiency (HIV-1, HIV-2)) because most viruses force cells to manufacture the enzymes required for DNA synthesis so that the viruses can generate sufficient nucleotides for viral replication or, in the case of retroviruses, for integration into the host genome. DNA tumor viruses suppress transcriptional down-regulation of the endogenous DNA precursor pathway enzyme TK1 during the eukaryotic cell cycle to improve conditions for their own replication. TK levels are not detectable in quiescent cells.

Virally-infected cells are selectively targeted by TK1 antibody and killed via complement dependent lysis (CDC) or antibody dependent cellular cytotoxicity (ADCC) by treating patients with anti-TK1 antibody according to preferred embodiments of the invention. Additionally, a number of viruses encode their own TK1 protein (HSV, EBV), which have been shown to have 70% homology to human TK1. We expect to detect viral TK1 on the surface of infected cells with the TK1 antibody disclosed herein or a similar antibody prepared as described herein and to selectively kill those cells by the same mechanism.

In some embodiments, the invention also pertains to enveloped viruses. The viral envelope, which is made up of host membrane (and some viral proteins), also expresses up-regulated TK1 on its surface due to viral infection. Thus, enveloped viruses are selectively targeted and killed and/or neutralized by anti-TK1 antibody mediated by complement mediated lysis of the viral envelope, by opsonization and phagocytosis by macrophages and other cells of the immune system which target the Fc region of anti-TK1 antibody, or by physical mechanisms that prevent the viral envelope from fusing with receptors on the membrane of other host cells and so preventing the virus from entering and infecting those cells. Consequently, the treatment methods disclosed herein also pertain to enveloped viruses.

In some embodiments, the cytotoxicity of TK1 antibody is enhanced by first treating patients with radiation therapy, which has been shown to up-regulate TK1 expression (because the DNA damage requires the generation of new nucleotides for DNA repair). After up-regulation of TK1 expression, the patient is treated with the TK1 antibody which binds the TK1 on the cell surface. By focusing the radiation therapy the toxicity of the antibody—if any—can be limited to the site of the tumor.

Embodiments of the present invention provide a biotherapeutic agent which is a monoclonal antibody to TK1. In some embodiments, the biotherapeutic agent is an immunoconjugate or immunotoxin, which includes a monoclonal antibody specific to TK1, linked to an effective amount of moiety, e.g., a polypeptide or a toxin, which has biological activity. Examples of useful biologically active moieties include ricin A chain immunotoxin, saporin, gelonin, Pseudomonas exotoxin or Pokeweed antiviral protein or an active fragment thereof. The activity of a preparation of pokeweed antiviral protein can be determined by methods which are described in U.S. Pat. No. 6,372,217 which is incorporated herein by reference. However, it is emphasized that it is not necessary in all embodiments to conjugate TK1 to an immunotoxin. The monoclonal antibody to TK1 alone may be pharmaceutically active.

It is preferred that the anti-TK1 biotherapeutic agent of the present invention employs the monoclonal antibody TK1 or a biologically active subunit, fragment or derivative thereof, which binds to TK1 present at the surface of virally-infected cells. A "biologically active" subunit or fragment of a monoclonal antibody has at least about 1%, preferably at least about 10%, and more preferably at least about 50%, of the binding activity of the monoclonal antibody.

These biotherapeutic agents are active both in vitro and in vivo, and are useful to treat diseases, such as certain viral infections, e.g., infections of HIV, influenza viruses, rhinoviruses, papovaviruses (e.g., human papilloma), adenoviruses, hepatitis virus, and the like. As used herein, the term monoclonal antibody (MAb) includes fragments, subunits and derivatives thereof. Preferably, the MAb is an anti-TK1 MAb.

The present invention provides a method to treat viral infection or inhibit viral replication in mammalian cells. The method comprises treating mammalian cells in vivo or treating a mammal having, or at risk of, a viral infection with an effective amount of either an antibody to TK1 or an immunoconjugate which includes an antibody to TK1. Moreover, the present TK antibody or TK1-immunoconjugate may also provide the basis for an effective method to inhibit other viral infections including, but not limited to HIV, influenza viruses, rhinoviruses, papovaviruses (e.g., human papilloma), adenoviruses, hepatitis virus, and the like. Methods are also disclosed herein for detection of increased expression of TK1 in a patient sample which indicates to the diagnostician the probability of the presence of viral infection. The results of these assays are used for further testing to provide a disease diagnosis.

In some embodiments, the patient is first treated with a MAb to TK that is immunologically inactive. This MAb binds to TK on viral infected cells and would also bind TK1 on normal cells should any express TK1. Next the patient is treated with an immunologically active anti-TK1 antibody to specifically bind to TK1 only on the surface of virally infected cells because of the anticipated contrast in the high level of TK1 expression between virally-infected cells and the low or non-existent level of TK1 expression in normal, rapidly-dividing cells. The infected cells are then killed by CDC or ADCC. It is emphasized that this method is only necessary if there is some cross-reactivity of the anti-TK1 antibody with normal cells.

In some embodiments, the anti-TK1 biotherapeutic agent is used in combination with a second anti-viral agent. The anti-viral agent may be a nucleoside/nucleotide reverse transcriptase inhibitor (nucleoside analog) such as zidovudine/lamivudine (Combivir®), emtricitabine (Emtriva®), emtricitabine (Epivir®), zalcitabine (Hivid®) zidovudine (Retrovir®), abacavir/zidovudine/lamivudine (Trizivir®), didanosine (Videx®, VidexEC®), tenofovir disoproxil fumarate (Viread®), stavudine (Zerit®), and abacavir (Ziagen®).

In some embodiments, a second anti-viral agent used in combination with the anti-TK1 biotherapeutic agent is a protease inhibitor such as amprenavir (Agenerase®), indinavir (Crixivan®), saquinavir (Fortovase®, Invirase®), fosamprenavir (Lexiva™), ritonavir (Norvir®), nelfinavir (Viracept®) and atazanavir (Reyataz™). In some embodiments a second anti-viral agent used in combination with the anti-TK1 biotherapeutic agent is an entry inhibitor such as enfuvirtide (Fuzdon™).

In some embodiments, a second anti-viral agent used in combination with the anti-TK1 biotherapeutic agent is a non-nucleoside reverse transcriptase inhibitor (non-nucleoside analog) such as delavirdine (Rescriptor®), efavirenz (Sustiva®), and nevirapine (Viramune®).

Without being bound to any theory, it is hypothesized that the above anti-viral agents operate by a mechanism similar to the anti-TK1 MAb. That is, cell proliferation requires DNA replication. Like the anti-TK1 antibody, these anti-viral agents interfere with the transformed cell's ability to replicate DNA and therefore are useful in a method of treating both cancer and viral infection. The methods described herein may be used generally to treat abnormal cell proliferation or abnormal states of elevated DNA replication, especially due to cancer or viral infection.

Multiple Sclerosis

Link Between Multiple Sclerosis and HSV

MS is a relapsing-remitting disease in which neurons of the CNS become demyelinated over time. Episodes are brought on by stress and illness. Similarly, HSV establishes a latent infection in nerve cells and only lyses them when the patient undergoes some sort of stress, i.e., emotional, physical (sunburn, contusion). HSV spread is limited to local infections because it binds HA which would explain why it takes so long for MS, which has been shown to be linked to HSV, to become truly debilitating. Because ~50% of the population is infected with some form of HSV it is possible that all people are susceptible to MS and that only the blood-brain barrier prevents its occurrence. Perhaps taking a drug that increases vascular permeability or an infection of the CNS would allow HSV to cross the blood-brain barrier and lead to MS via HSV.

The current Multiple Sclerosis paradigm is that it is an autoimmune disorder in which T cells of the CNS attack the neurons of the CNS. We predict that T cells are not attacking self antigens, but are attacking human or viral TK1, which we expect will be constitutively expressed on neurons. The similarity between viral TK1 and human TK1 could elicit an immune response to both enzymes, which would then lead to a true autoimmune disorder. This event (recognition of self, even though accidental) would correlate with disease progression, probably rapid, and the worst symptoms of MS; paralysis, blindness, loss of muscle control, death.

Another study (Intranasal herpes simplex virus type 2 inoculation causes a profound thymidine kinase dependent cerebral inflammatory response in the mouse hindbrain. Boivin G, Coulombe Z, Rivest S. Eur J Neurosci. 2002 July.; 16(1):29-43) shows that intranasal herpes simplex virus type 2 inoculation causes a profound thymidine kinase dependent cerebral inflammatory response in the mouse hindbrain. The herpes simplex virus (HSV) has the ability to replicate in the central nervous system (CNS), which may cause fatal encephalitis. The activity of the nuclear factor kappa B (NF-kappa B) and the pattern of cytokine/chemokine gene expression across the brain of HSV-infected mice indicate a role for the viral thymidine kinase (TK) in mediating these effects. Animals infected with the TK-competent virus exhibit first signs of infection at day 5 post-inoculation, whereas severe signs of sickness are observed between day 6 and 8. A robust signal for the TK gene and its encoding protein is detected selectively within the regions that exhibit expression of the immune molecules. In contrast, animals that receive the TK-deficient virus do not show any signs of sickness or cerebral inflammation or HSV replication within the cerebral tissue. There is clear evidence that HSV-2 has the ability to trigger a profound inflammatory response in a pattern that follows the viral TK-dependent HSV replication in neurons. Such neurovirulence occurring in the hindbrain is directly responsible for neurodegeneration and leads to the cerebral innate immune response, which in turn could play a key role in fatal HSV-2-induced encephalitis.

Emotional disturbances are common in MS and consist of disturbances of mood and affect. The important mood disorders are Major Depressive Disorder, Dysthymic Disorder, Bipolar Disorder, Panic Disorder, and Generalized Anxiety Disorder.

Their relationship to MS is multi-factorial and complex, and the extent to which they are direct consequences of the disease process or psychological reactions to it remains unclear. Whatever their cause, however, the symptoms of mood disorders in people with MS are no different from the symptoms of mood disorders in people without MS, and respond just as well to standard treatments. The disorders of affect are euphoria, pathological laughing and weeping, and other Frontal Lobe Syndromes. These disorders result from demyelination and are some of the most characteristic symptoms of MS, and have the same implications for treatment as do other aspects of the disease. Mood and affective disturbances can cause enormous pain and suffering and lead to significant disruption of family, work, and social life.

Monoclonal Antibodies

Monoclonal antibodies (MAbs) are produced in accordance with one embodiment of the present invention by the fusion of spleen lymphocytes with malignant cells (myelomas) of bone marrow primary tumors. Milstein, Sci. Am., 243, 66 (1980). The procedure yields a hybrid cell line, or hybridoma, arising from a single fused cell hybrid, or clone, which possesses characteristics of both the lymphocytes and myeloma cell lines. Like the lymphocytes (taken from animals primed with sheep red blood cells as antigens), the fused hybrids or hybridomas secrete antibodies (immunoglobulins) reactive with the antigen. Moreover, like the myeloma cell lines, the hybrid cell lines are immortal. Specifically, whereas antisera derived from vaccinated animals are variable mixtures of antibodies which cannot be identically reproduced, the single-type of immunoglobulin secreted by a hybridoma is specific to one and only one determinant on the antigen, a complex molecule having a multiplicity of antigenic molecular substructures, or determinants (epitopes). Hence, monoclonal antibodies raised against a single antigen may be distinct from each other depending on the determinant that induced their formation. However, all of the antibodies produced by a given clone are identical. Furthermore, hybridoma cell lines can be reproduced indefinitely, are easily propagated in vitro and in vivo, and can yield monoclonal antibodies in extremely high concentrations.

Monoclonal antibodies have largely been applied clinically to the diagnosis and therapy of cancer, the modulation of the immune response to produce immunosuppression for treatment of autoimmune and graft versus host diseases (GVHD) and for prevention of allograft rejection. Human monoclonal antibodies have also been applied clinically against cytomegalovirus, Varicella zoster virus, and the various specific serotypes of *Pseudomonas aeruginosa, Escherichia coli,* and *Klebsiella pneumoniae.*

Some monoclonal antibodies useful in the present invention are produced using well known hybridoma fusion techniques (G. Kohler and C. Milstein, Eur. J. Immunol., 6, 511 (1976); M. Shulman et al., Nature, 276, 269 (1978)). As indicated above, the present invention uses a monoclonal antibody directed against TK1.

U.S. Pat. No. 5,698,409, which is incorporated herein by reference, describes a purified mammalian thymidine kinase 1 (TK1) from Raji cells. Raji cells are an immortalized human lymphoma cell line, available from ATCC as cell line #CCL-86. U.S. Pat. No. 5,698,409 also describes a monoclonal antibody to TK1 which not only binds to TK1 but also inhibits TK1 activity. Specific anti-TK1 antibody monoclonal producing hybridomas are available as ATCC HB 11432, HB 11433 and HB 11434.

In some embodiments, it is preferred to humanize the anti-TK1 MAb. The humanized antibody can comprise portions derived from an immunoglobulin of nonhuman origin with the requisite specificity, such as a mouse, and from immunoglobulin sequences of human origin (e.g., a chimeric immunoglobulin), joined together chemically by conventional techniques (e.g., synthetic) or prepared as a contiguous polypeptide using genetic engineering techniques (e.g., DNA encoding the protein portions of the chimeric antibody can be expressed to produce a contiguous polypeptide chain). Another example of a humanized immunoglobulin of the present invention is an immunoglobulin containing one or more immunoglobulin chains comprising a CDR of nonhuman origin (e.g., one or more CDRs derived from an antibody of nonhuman origin) and a framework region derived from a light and/or heavy chain of human origin (e.g., CDR-grafted antibodies with or without framework changes). Chimeric or CDR-grafted single chain antibodies are also encompassed by the term humanized immunoglobulin.

Also included within the invention are humanized antibodies which have been veneered or reshaped. For example, the rodent variable region is compared to the consensus sequence of the protein sequence subgroup to which it belongs and the selected human constant region accepting framework is compared with its family consensus sequence. Idiosyncratic residues are replaced by more commonly occurring human residues.

Such humanized immunoglobulins can be produced using synthetic and/or recombinant nucleic acids to prepare genes encoding the desired humanized chain. For example, in U.S. Pat. No. 4,816,567 (incorporated herein in its entirety by reference) altered and native immunoglobulins, including constant-variable region chimeras, are prepared in recombinant cell culture. The immunoglobulins contain variable regions which are immunologically capable of binding predetermined antigens. Methods are provided in U.S. Pat. No. 4,816,567 for refolding directly expressed immunoglobulins into immunologically active form (See also, U.S. Pat. No. 6,331,415; incorporated in its entirety by reference). In other examples, nucleic acid sequences coding for humanized variable regions can be constructed using PCR mutagenesis methods to alter DNA sequences encoding a human or humanized chain, such as a DNA template from a previously humanized variable region (see e.g., Kamman, M., et al., Nucl. Acids Res., 17: 5404 (1989)); Sato, K., et al., Cancer Research, 53: 851-856 (1993); Daugherty, B. L. et al., Nucleic Acids Res., 19(9): 2471-2476 (1991); and Lewis, A. P. and J. S. Crowe, Gene, 101: 297-302 (1991)). Using these or other suitable methods, variants can also be readily produced. In one embodiment, cloned variable regions can be mutagenized, and sequences encoding variants with the desired specificity can be selected (e.g., from a phage library; see e.g., Krebber et al., U.S. Pat. No. 5,514,548; Hoogenboom et al., WO 93/06213, published Apr. 1, 1993; Knappik et al., WO 97/08320, published Mar. 6, 1997)).

Alternatively, humanized antibodies may be conveniently prepared by injection of purified TK1 into SKID mice or other SKID animal which have accepted xenografts of adult human peripheral blood leukocytes as described in U.S. Pat. No. 5,476,996, which is incorporated herein by reference in its entirety. By this treatment, human immune function is introduced into the SKID animal which can be used to produce humanized antibodies.

Immunotoxins

Certain embodiments of the invention include the use of an immunotoxin linked to the anti-TK1 MAb. Several requirements must be fulfilled for an immunotoxin to be effective. First of all, the immunotoxin should be specific and should not react with tissues that do not express the target antigen to the extent that it is detrimental to the target mammal. Pastan et al., Cell, 47, 641 (1986). Binding to tissues that do not express antigen can be reduced by removal of the nonspecific natural cell-binding subunits or domains of the biotherapeutic moiety, e.g., a plant glycoprotein toxin or antiviral agent. Furthermore, because plant glycoprotein toxins contain mannose oligosaccharides that bind to cells of the reticuloendothelial system and, in some cases, also contain fucose residues that are recognized by the receptors on hepatocytes, deglycosylation of plant toxins may be required to, avoid rapid clearance and potential cytotoxic effects on these cells. Secondly, the linkage of the toxin to the antibody should not substantially impair the capacity of the antibody to bind to the antigen. Third, the immunotoxin must be effectively internalized into the endosomic vesicles. Thus, toxins directed by monoclonal antibodies to surface receptors that are normally internalized may be more active than those directed toward noninternalizing cell surface molecules. Fourth, the active component of the toxin must translocate into the cytoplasm. Finally, for in vivo therapy, the linkage between the MAb and the toxin must be sufficiently stable to remain intact while the immunotoxin passes through the tissues of the mammal to its cellular site of action.

The activity of an immunotoxin is initially assessed by measuring its ability to kill cells with target antigens on their surfaces. Because toxins act within the cells, receptors and other surface proteins that naturally enter cells by endocytosis usually are appropriate targets for immunotoxins, while surface proteins that are fixed on the cell surface are not. However, if several antibodies recognizing different epitopes on the same cell surface protein are available, it is useful to test them all. This is because some antibodies, perhaps by producing a conformational change in the target protein, may more efficiently induce internalization or direct intracellular routing to an appropriate location for toxin translocation. May et al., Cell Immunol., 135, 490 (1991). Also, if the receptors are efficiently internalized, it is possible to employ an immunotoxin that does not bind as strongly to the receptor, due to the chemical modification(s) needed to prepare the immunotoxin. Willingham et al., Proc. Natl. Acad. Sci. USA, 84, 2474 (1987).

Toxins

An array of toxins of bacterial and plant origin have been coupled to MAbs for production of immunotoxins. The strategy is to select from nature a cytotoxic protein and then to modify the cytotoxic protein so that it will no longer indiscriminately bind and kill normal cells, but will instead kill only the cells expressing the antigen bound by the MAb. To be optimally effective, such an approach requires that internalization of relatively small numbers of cytotoxic molecules be lethal to target cells, as there are limited receptor sites on the cell surface for a given MAb. The toxins produced by certain bacteria and plants that inactivate cellular protein synthesis meet this criteria as, unlike most chemotherapeutic agents which act in a stoichiometric manner, they are catalytic in their lethal activity. In general, less than ten toxin molecules in the cytoplasm of a cell are sufficient to kill the cell.

Two classes of toxins that inactivate protein synthesis have been widely employed in the construction of immunotoxins. The first class consists of intact toxins, such as intact ricin. These toxins cannot be safely applied in vivo because of lethal toxicity. The second group of toxins are referred to as hemitoxins. Lethally inhibiting protein synthesis in a complementary manner, hemitoxins covalently modify the ribosome such that it can no longer productively interact with elongation factor 2. This latter family of toxins includes pokeweed antiviral protein (PAP), ricin, abrin, gelonin, saporin, and alpha-sarcin. The ribosome inactivating proteins derived from plants consist of either two chains, including a binding chain and catalytic chain (e.g., ricin), or a single catalytic chain alone (e.g., PAP or saporin).

In certain embodiments, anti-TK1 antibody immunotoxins for use in the present method are formed by linking an effective cytotoxic or antiviral amount of immunotoxin molecules to each molecule of anti-TK1 antibody. For example, a reagent useful in the practice of the invention includes one to two immunotoxin molecules per anti-TK1 antibody molecule. Preferably, a composition of the invention includes about a 1:1 mixture of a) one molecule of immunotoxin/molecule of anti-TK1 antibody, and b) two molecules of immunotoxin/molecule of anti-TK1 antibody. Preferably, a composition of the invention contains mainly 1 or 2 immunotoxin molecules per intact anti-TK1 monoclonal antibody molecule, free anti-TK1 monoclonal antibody, and free immunotoxin.

Modes of Administration of Anti-TK1 MAb or Anti-TK1 Antibody Biotherapeutic Agent The anti-TK1 MAb or anti-TK1 antibody biotherapeutic agent of the invention, or a combination thereof, can be formulated as a pharmaceutical composition and administered to a human or other mammal infected with a virus, preferably as a unit dosage form comprising an effective amount of one or more of the anti-TK1 MAb or anti-TK1 antibody, optionally coupled to an immunotoxin, in combination with a pharmaceutically acceptable carrier or vehicle, and/or in combination with other therapeutic agents.

Dosage Forms

It is preferred that the anti-TK1 MAb or anti-TK1 antibody biotherapeutic agent of the present invention be parenterally administered, i.e., intravenously, or subcutaneously by infusion or injection. Solutions or suspensions of the biotherapeutic agent can be prepared in water, or a physiological salt solution such as isotonic saline or PBS, optionally mixed with a nontoxic surfactant.

Although it is preferred that the anti-TK1 MAb or anti-TK1 antibody biotherapeutic agent be administered as a liquid composition as described herein, it can be administered with a variety of other carriers. For example, dispersions can also be prepared in glycerol, liquid polyethylene glycols, DMA, vegetable oils, triacetin, and mixtures thereof. Under ordinary conditions of storage and use, these preparations may contain a preservative to prevent the growth of microorganisms. Additionally, more specific delivery of the anti-TK1 MAb or anti-TK1 antibody biotherapeutic agent to the lungs may be accomplished via aerosol delivery systems.

The compositions suitable for injection or infusion can include sterile aqueous solutions or dispersions or sterile powders comprising the anti-TK1 MAb or anti-TK1 antibody biotherapeutic agent which are adapted for the extemporaneous preparation of sterile injectable or infusible solutions or dispersions. In all cases, the ultimate composition must be sterile, fluid and stable under the conditions of manufacture and storage. The liquid carrier or vehicle can be a solvent or liquid dispersion medium comprising, for example, water, ethanol, a polyol (for example, glycerol, propylene glycol, and liquid polyethylene glycols, and the like), vegetable oils, nontoxic glycerol esters, lipids (for example, dimyristoyl phosphatidyl choline) and suitable mixtures thereof. The proper fluidity can be maintained, for example, by the formation of liposomes, by the maintenance of the required particle size in the case of dispersion or by the use of nontoxic surfactants. The prevention of the action of microorganisms can be accomplished by various antibacterial and antifungal agents, for example, parabens, chlorobutanol, phenol, sorbic acid, thimerosal, and the like. In many cases, it will be desirable to include isotonic agents, for example, sugars, buffers or sodium chloride. Prolonged absorption of the injectable compositions can be brought about by the inclusion in the compositions of agents delaying absorption, for example, aluminum monostearate hydrogels and gelatin.

Sterile injectable or infusable solutions are prepared by incorporating the anti-TK1 MAb or anti-TK1 antibody biotherapeutic agent in the required amount in the appropriate solvent with various of the other ingredients enumerated above, and as required, followed by filter sterilization. In the case of sterile powders for the preparation of sterile injectable or infusable solutions, the preferred methods of preparation are vacuum drying and the freeze drying techniques, which yield a powder of the active ingredient plus any additional desired ingredient present in the previously sterile-filtered solutions.

Furthermore, suitable formulations for the anti-TK1 MAb or anti-TK1 antibody biotherapeutic agent of the present invention include those suitable for oral, rectal, nasal, topical (including, ocular, and sublingual) or vaginal administration or in a form suitable for administration by inhalation or insufflation. The formulations may be prepared by any of the methods well known in the art of pharmacy. Such methods include the step of bringing into association the biotherapeutic agent with liquid carriers or finely divided solid carriers or both and then, if necessary, shaping the product into the desired formulation.

Pharmaceutical formulations suitable for oral administration may conveniently be presented as discrete units such as capsules, sachets, or tablets, each containing a predetermined amount of the active ingredient; as a powder or granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The biotherapeutic agent of the present invention may also be formulated for intra-nasal or ocular administration. In this form of administration, the active ingredient may be used as a liquid spray or dispersible powder or in the form of drops. Drops, for example, eyedrops, may be formulated with an aqueous or non-aqueous base also comprising one or more dispersing agents, solubilizing agents or suspending agents. Liquid sprays are conveniently delivered from pressurized packs.

For administration by inhalation, the biotherapeutic agent is conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation of insufflation, the biotherapeutic agent may take the form of a dry powder composition, for example, a powder mix of the compound or a suitable powder base such as lactose or starch. The powder composition may be presented in unit dosage form in, for example, capsules or cartridge or e.g., gelatin or blister packs from which the powder may be administered with the aid of an inhaler of insufflator.

Additionally, the anti-TK1 MAb or anti-TK1 antibody biotherapeutic agent of the present invention is well suited to formulation in controlled release dosage forms. The formulations can be so constituted that they release the active dry ingredient only or preferably in a particular physiological location, optionally over a period of time. The coatings, envelopes, and protective matrices may be made, for example, from polymeric substances or waxes. The compounds can also be delivered via patches for transdermal delivery, subcutaneous implants, infusion pumps or via release from implanted depot sustained release dosage forms.

Dosages

The dosage of the biotherapeutic agents in the compositions of the invention can be varied widely, in accord with the size, age and condition of the mammal and the disease. Dosages are administered with a frequency based on the plasma half life of anti-TK1 MAb or anti-TK1 antibody biotherapeutic agent in a given patient. Higher doses can be employed in some cases, and the doses can readily be adjusted to provide appropriate amounts of the biotherapeutic agent to children.

EXAMPLES

Example 1

Assay of Raji Cells for TK1 Activity

Preparation of TK1 and TK1 monoclonal antibody was performed essentially as described in U.S. Pat. No. 5,698,409, which is incorporated herein by reference. A crude cell extract was prepared from Raji cells (human Burkitt's lymphoma, American Type Culture Collection (ATCC) CCL 86) as follows. Approximately $10^{11}$ to $10^{12}$ exponentially-growing Raji cells were harvested by centrifugation from the growth medium. The pelleted cells were separated from the supernatant and resuspended in 1-2 mls of extraction buffer containing 0.02M Tris-HCl, pH 7.8, 0.05 M $MgCl_2$, and 0.2 mM KCl. The cell suspension was subjected to three freeze-thaw cycles in liquid nitrogen and a 37° C. water bath. The ruptured cell suspension was then centrifuged at 30,000×g for 30 minutes at 4° C. to pellet cellular debris. The supernatant, containing about 50 mg/ml of protein, including TK and other soluble enzymes, was decanted from the pellet and stored frozen at −20° C.

To perform TK assays, 0.2 ml of the crude extract was mixed with an equal amount (0.2 ml) of an assay mixture containing 0.02M Tris-HCl (pH 7.8), $2 \times 10^{-6}$ M $[^3H]$-thymidine (85 curies per mmole), 0.002 M $MgCl_2$, 0.2M KCl, 0.1M $NH_4Cl$, 0.005M mercaptoethanol, and 0.004M ATP (adenosine triphosphate).

The assay reactions were incubated at 37° C. in a water bath. After 30 minute and 60 minute incubation periods, 0.025 ml samples were removed and spotted onto Whatman DE-81 discs and allowed to dry. The filter discs were washed three times with 0.01M formate for 5 minutes each time, rinsed with distilled water for 5 minutes, followed by rinsing with methanol, and then transferred to scintillation vials containing 4 mls of scintillation counting fluid for measurement of $^3H$ radioactivity.

Example 2

Partial Purification of TK1

TK enzyme was partially purified from the crude extract of Raji cells of Example 1 by DEAE-cellulose anion exchange chromatography. To obtain the largest yields of TK protein, it is desirable that the cells be in the exponential growth phase when harvested. The protein content of the crude extract was determined using the well-known Bradford assay. A total of about 1.0-2.0 grams of protein from the crude extract was added to a DEAE-cellulose column and washed with 10 void volumes of 0.1M Tris-HCl (pH 8.0) using gravimetric flow. The column was eluted with 0.5M Tris-HCl (pH 8.0), and 1.0 ml fractions were collected.

A chromatograph of the absorbance measured at 280 nm as a function of elution time was produced. Aliquots of the collected fractions were assayed for TK1 activity generally as described in Example 1. Multiple runs were pooled and were concentrated using an Amicon protein concentrator.

Example 3

Purification by FPLC

An FPLC column (Pharmacia MONO-Q 5/5 anion exchange column) was loaded with 0.1 ml of the concentrated DEAE-cellulose fraction, described above, containing about 1 mg protein, and voided with 10 volumes of Buffer A (50 mM Tris-HCl pH 8.0). A programmed gradient was set up to gradually increase the concentration of Buffer B (1.0M NaCl, 50 mM Tris-HCl, pH 8.0) from 0-100% over 20 minutes running at a constant flow rate of 1.0 ml/min.

The protein was detected as it eluted from the column by absorbance at 280 nm. Fractions containing the 280 nm absorbance peaks were collected and assayed for TK1 activity as described previously herein.

The fractions having TK1 activity from several runs were collected, pooled and concentrated. This partially purified, pooled sample was then re-run on the MONO-Q column with a lower gradient. One-tenth ml portion of pooled sample containing about 1 mg protein was loaded on the MONO-Q column as before. For this second run, the gradient was started at 5% of Buffer B and ran to 40% Buffer B over 35 minutes at 1.0 ml/min.

A chromatogram of absorbance vs. elution volume for the second sequential MONO-Q run was produced. Fractions containing 1.0 ml of elutant were again collected as determined by assay for TK1 activity.

A third sequential MONO-Q run was performed on protein precipitated and pooled from the second column above. The running conditions were further changed by slowing the flow rate and further decreasing the gradient. A gradient of 5% Buffer B to 30% Buffer B was run at 0.5 mls/min. For this run, 0.5 ml fractions were collected.

Example 4

Production of Monoclonal Antibodies Binding to TK1

Hybridoma cell lines producing antibodies to TK were produced by methods generally known in the art, but with certain modifications. The description of the development of monoclonal antibodies using a particular hybridoma cell line is only exemplary. Embodiments of the invention contemplate the use of a battery of clones produced by various means such as the use of hybridoma cell lines and other recombinant techniques.

TK1 was prepared as described above. A dose of 100 μg of TK1 suspended in 50 μl of phosphate buffered saline (PBS) and 50 μl complete Freund's adjuvant was given intraperitoneally (I.P.) to each of a group of female BALB/c mice, 5-6 weeks old. Two weeks later, a second immunization was given that was identical to the first.

Two weeks following the second immunization with semi-pure TK1, an intrasplenic injection was given which contained 10 μg of pure active TK1 (prepared as described above) suspended in 100 μl of PBS. The mice were anesthetized with sodium pentobarbital (65 mg/ml) which was diluted by adding 6.7 mls to 93.3 mls of PBS. Each mouse was given 10 μl/gram of body weight I.P. Surgical intervention was performed using a scalpel and forceps, and the spleen was gently teased out for administration of the antigen. Several areas of the spleen were injected to ensure uniform distribution of the antigen. The wound was closed with metal sutures and the mice were placed under a heating lamp for 1-2 hours.

Seventy-two hours following the intrasplenic injection, the mice were sacrificed using ether and the spleen was removed. Before the mice were killed, blood was removed and the serum tested to ensure that the mice were mounting an immune response to the TK1 protein. The B cells were isolated from the spleen for fusion with an immortal myeloma cell line.

The cell line used for the fusion partner was a self-fused Sp2/0 line designated FO which was purchased from ATCC. It is a derivative of P3-X63-Ag8. This line is an immortal myeloma mouse cell line that is fast growing and a non-secretor (heavy or light chain immunoglobulins). The fusion of FO and activated spleen cells was performed generally as known in the art. One spleen containing about $1 \times 10^8$ cells was used per fusion. After the fusion was terminated, the fusion cell suspension was seeded into 96-well microtiter plates which had been seeded a day earlier with 3,000 to 6,000 mouse macrophages per well as feeder cells.

HAT selection medium was used to select only fusion products. Wells were marked for growth and gradually weaned out of HAT and into regular media. By this time the only surviving cells were hybridomas obtained by fusion of B-cells and FO cells. A total of about 500 colonies representing fusion products resulted from each fusion.

For use in tests with patient samples, the selected antibody-producing cell lines were passaged and supernatant was aseptically collected over a period of three months. Antibodies were purified by precipitating the supernatants with ammonium sulfate followed either by gel filtration chromatography or by DEAE-cellulose chromatography (diethylaminoethyl cellulose, obtained from Whatman International, Maidstone, Kent, UK under the tradename SEPHADEX). The antibodies were purified by standard methods and conjugated with either HRP-peroxidase or alkaline phosphatase (Bio-Rad). Such procedures are described in ANTIBODIES: A Laboratory Manual, by Harlowe and Lane, 1988.

Example 5

Production of Humanized Monoclonal Antibodies Binding to TK1

Human peripheral blood leukocytes are injected intraperitoneally into SCID mice as described in U.S. Pat. No. 5,476,996, which is incorporated herein by reference. About 2 weeks later, the SKID mice are immunized with human TK1. MAb are then obtained as described above in Example 4 or by recombinant techniques.

Example 6

Western Blot Using Anti-TK1 Antibody

A Western blot was performed using an anti-TK1 antibody prepared according to the invention. The Western blots were prepared by procedures similar to those described in Current Protocols in Immunology, Vol. 1, publ. Wiley-Interscience, New York (1991).

FIG. 1 shows a Western blot of TK1 specificity for clone 14F2. The samples were separated using a native or a partial denaturing 12% polyacrylamide gel. Polypeptides were transferred onto a nitrocellulose filter and probed with MAb from clone 14F2. A conjugate antibody solution containing goat anti-mouse IgG (H1L chains) horseradish peroxidase was used to visualize MAb binding. (a) Lane 1, purified TK1, native sample, Ponceau S staining; Lane 2, purified TK1, native sample, Western blot. (b) Lane 1, purified TK1, partial denatured sample, Ponceau S staining; Lane 2, Purified TK1, partial denature sample, Western blot; Lane 3, Raji cell extract, partial denature sample, Western blot; Lane 4, Hela cell extract, partial denature sample, Western blot.

Example 7

Inhibition of TK1 Activity by Selected Monoclonal Antibodies

Raji cells ($1 \times 10^6$) were harvested by centrifuging the cells at 1500 rpms for 10 minutes. The supernatant was discarded, 1 ml of enzyme mix (1:10 0.02% β-mercaptoethanol:Tris-HCl pH 7.5) was added and the mixture was frozen in liquid nitrogen. The cells were then thawed in a 37° C. water bath. The freeze/thaw step was repeated three times. The samples were then centrifuged at 14,000 rpms at 4° C. for 75 minutes to remove cell membranes. The cell lysate was removed from the eppendorf tube, leaving the pellet in the bottom of the tube. 25 μl of Raji cell extract was placed in each of 6 eppendorf tubes.

Figure 2:
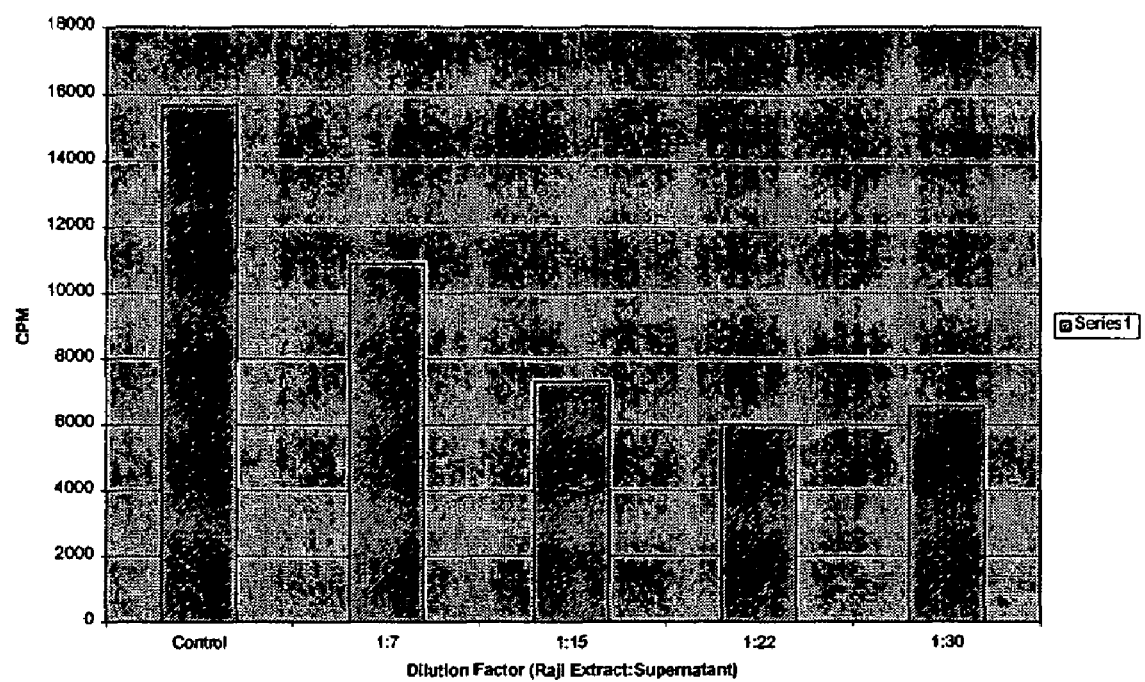
FIG. 2 shows inhibition of TK1 activity by MAb 5G11 at a series of dilutions of the MAb.

Dilutions of fresh hybridoma media:hybridoma supernatant were made totaling 125 μl in the following proportions: 1:2, 1:4, 1:16, 1:32, 1:64. As a control, 125 μl of hybridoma media was used. The 125 μl dilution volumes or control were added to each of the 6 eppendorf tubes. Each of the tubes was assayed for thymidine kinase activity using the thymidine kinase radioassay described above. The greater the inhibition by the antibodies in the hybridoma supernatant, the lower the thymidine kinase activity The results are shown in FIG. 2. The radioactivity of the control is almost 16,000. Incorporation of radioactivity drops as the amount of TK1 antibody in the sample is increased. At a 1:22 dilution the activity is down to 6,000 cpm or about ⅓ of the TK1 activity of the control in the absence of TK1 antibody. This shows that when the Mab to TK1 binds within the catalytic site, enzymatic activity of TK1 is inhibited in the presence of the MAb. However, it is emphasized that it is not necessary to inhibit TK1 activity in order to affect cell proliferation by binding of the anti-TK1 antibody to TK1 on the surface of virally-infected cells.

Example 8

Detection of Active TK1 in Samples from HIV Infected Patients Using Anti-TK1 Antibody For the determination of serum TK levels in human subjects, fresh samples of peripheral venous blood are collected from the subjects. Serum and mononuclear leukocytes are separated from each sample by conventional methods, and the separated samples are stored frozen until analysis. TK levels in tissues can be determined by preparing an extract of TK from samples of fresh tissue using a method similar to that for the crude extract of Raji cells of Example 1. Preferably, the protein content of the sample is determined so that the amount of TK can be correlated with the amount of total protein in the tissue. An immunoprecipitation assay using the desired anti-TK antibody can then be performed on the extract.

TK activity is elevated in the serum of patients with certain viral infections. For the most part, sera of patients with viral infection show an elevated TK1 activity compared to control patients.

Serum samples are obtained from HIV—infected patients. Each sample is assayed for TK activity by a method like that of Example 1. The same samples are then quantitated blindly on an ELISA test with anti-TK1 antibody using different serum dilution levels. TK1 activity measurements correlate with the antibody binding data and the standard TK1 activity assay. Anti-TK1 antibody can be used to evaluate the serum level of TK1 activity in human subjects. Further, serum from a healthy (non-viral-infected) individual binds much less anti-TK1 antibody as compared to serum from an HIV-infected patient. Thus, the anti-TK1 antibody is useful to distinguish between serum of HIV-infected individuals and serum from healthy non-infected individuals.

Example 9

Diagnostic and Prognostic Test which Utilize Anti-TK1 Antibodies

Additionally, this invention contemplates development of specific tests, which utilize anti-TK1 antibodies to diagnose the presence of a viral infection such as HIV, HSV, EBV, papilloma and polyoma viruses. An example of this embodiment includes the use of IFA and ELISA based non-invasive monoclonal TK1 tests that indicate both early viral infection and provide clinical prognosis during treatment.

For example the invention contemplates an IFA based diagnostic test designed to detect TK1 in patient tissue samples and blood, using a fluorescent compound to detect the binding of antigen and antibody. The anti-TK1 antibody is labeled with the fluorescent compound and its presence is detected using a fluorescence microscope. This IFA test is used to detect the presence and quantity of TK1 in the patient's tissue, which is matched against a standard curve to provide the clinician with diagnostic and prognostic information.

This example comprises the following steps. Techniques generally known in the art are used to conduct all the following protocols. The patient sample is prepared, which is normally a tissue section, cytology smear, or impression smear from the patient but is not limited to these particular types of samples. The unknown sample is fixed to a slide. Fluorescent labeled anti-TK1 antibodies and the patient sample are combined to allow the antibody to bind to TK1 (if TK1 is present). Subsequently, the slides are washed to remove everything but the antibodies bound to TK1. After washing antibody-antigen binding is detected by observing the slide under a fluorescence microscope. Samples testing positive for the antigen of interest, in this example TK1, would fluoresce, while samples testing negative for the antigen of interest would not. The sample slide is then compared to a standard curve.

Additionally, this invention contemplates development of other specific tests, which utilize anti-TK1 antibodies to diagnose a viral infection. An additional example of this embodiment uses an ELISA based diagnostic test to detect TK1 in a patient's serum sample, which is optimized to run on any standard plate reader. In the ELISA based diagnostic exam contemplated by this embodiment, the measured antigen is TK1. One of the methods that is followed includes the following steps. An antibody that reacts with the TK1 is firmly attached to the surface of the microtiter plate. The patient serum sample being tested is added and incubated, which allows the antibodies on the plate to bind with TK1. The plate is then washed to remove everything but the TK1 bound to antibodies. A second antibody that reacts with another epitope on TK1 and that is covalently attached to an enzyme is added and incubated with the antibody-TK1 complex in second step above. The plate is then washed again to remove everything but the TK1 bound to antibodies. A colorless substrate of the enzyme is added. If TK1 is present in the patient serum sample, the enzyme-linked antibodies will convert the colorless substrate to a colored product. The fluorescence of the plate is measured and compared to a standard curve. The presence of TK1 indicates the likelihood of viral infection. Alternatively, a viral infection may be detected and located using a radio opaque dye coupled to TK1 antibody which is then detected by PET, CT, or MRI.

Example 10

Flow Cytometer

Assays demonstrate that selected monoclonal antibodies bind specifically to cells producing TK1. Flow Cytometer plots are utilized to further characterize the ability of anti-TK1 antibodies to specifically target virally-infected cells.

Blood is drawn from control patients and from patients known to be infected with a virus. Both the controls and the viral infected samples are run through the Flow cytometer to provide baseline levels. For each sample, two 12×75 mm test tubes are labeled, one for the monoclonal antibody and the other for the appropriate control. Cells ($1 \times 10^6$) from the cell preparation are placed in each test tube and centrifuged at 2-8° C. at 400-450×g for 4 min. The supernatant is aspirated and discarded.

Then 200 µL monoclonal antibody working solution or 200 µL of control working solution is placed into the appropriately labeled test tubes. The reactions are vortexed gently. The reactions are incubated at 2-8° C. for 30-35 min. Following incubation each reaction mixture is washed with 1 mL of 2-8° C. wash medium and centrifuged at 2-8° C. at 400-450×g for 4 min. Each reaction is aspirated carefully and the supernatant is discarded. A vortex is used subsequently to disrupt cell pellets. The wash steps that followed incubation are repeated. After the second wash, the samples are aspirated carefully and the supernatant is discarded. Then 200 mL of GAM-FITC working solution or Avidin d-FITC working solution (for Biotin-labeled) is added to each cell pellet. The cell pellets are gently disrupted using a vortex. The cells are incubated at 2-8° C. for 30-35 min. At the end of 30 min., the cells are washed three times with 1 mL of 2-8° C. resuspension medium. Each centrifugation is carried out at 400-450×g for 4 min at 2-8° C. The sample is then aspirated carefully and the supernatant is discarded. The cell pellets are then gently disrupted using a vortex. The steps following the second incubation are repeated twice. After the third wash, the cells are resuspended by adding 1 mL of 2-8° C. resuspension medium to each test tube. The samples are transferred into appropriate containers for flow cytometry or fluorescence microscopy analysis. To ensure maximum viability, the stained cells are analyzed promptly.

When normal cells are incubated with the anti-TK antibody, the percent of cells counted by the flow cytometer is similar to unlabeled cells indicating that the normal cells do not express TK1. When the viral infected cells are incubated with the anti-TK1 antibody, these cells are detected by flow cytometry as the viral-infected cells express TK1 and are detected by the method. Consequently, higher cell counts are obtained.

Example 11

Membrane Bound Protein Staining Protocol

Blood is harvested from HIV-infected patients in heparin tubes. The blood samples are diluted 1:2 dilution with balanced salt solution (PBS). 5 mls of phicol is placed in the bottom a 15 ml conical vial (one conical vial for every 7 mls of diluted blood). The conical vials are placed in a centrifuge at 1300 rpms for 20 minutes. After centrifugation is complete, a 1 ml pipet is used to remove the buffy layer that is suspended on the surface of the phicol. Up to 7 mls of the lymphocyte solution is placed into a fresh 15 ml conical vial and diluted 1:2 using PBS. The sample is again centrifuged at 1500 rpms for 10 minutes. The washing step is repeated two times.

After washing the cells twice, the cells are resuspended in 3% formaldehyde solution for 10 minutes on ice (this step fixes the cells, and inhibits cell activation and interaction). After ten minutes, the cells are centrifuged at 1500 rpms for 10 minutes. The cells are removed from the centrifuge and the supernatant is aspirated. The cells are resuspended in 2 mls of PBS and centrifuged again at 1500 rpms for 10 minutes. The cells are washed two more times.

After washing the cells for the second time, the supernatant is poured off, leaving a small amount of liquid in the bottom of the conical vial. 10 µl of FC block is added to the cells and the cells are resuspended in a small amount of PBS and the FC block.

The cells are incubated on ice for 10 minutes. After 10 minutes the cells are removed from the ice and resuspended in 2 mls of PBS. The mixture is centrifuged at 1500 rpms for 10 minutes. The cells are washed two more times.

The cells are removed from the centrifuge and resuspended in 10 mls of supernatant from a hybridoma cell line. The cells are incubated on ice and in the dark for 1.5 hours. The cells are removed from ice and centrifuged at 1500 rpms for 10 minutes. The cells are washed two more times.

The secondary antibody is diluted appropriately. 200 µs of secondary antibody is added to each cell pellet after the final wash and incubated on ice and in the dark for 1 hour. After 1 hour the cells are removed from ice and resuspended with 2 mls of PBS. The resuspended cells are centrifuged at 1500 rpms for 10 minutes and the supernatant is removed by aspiration. The cell wash is repeated 3 times. The washed cells are resuspended in 100 µls and the solution may be kept until ready to view.

10 µl are placed on a clean microscope slide and covered with a glass cover slip. It is observed that the cells obtained from the HIV infected patients are stained while the cells from the uninfected control are not stained.

Example 12

CDC Experiment with HIV Infected Cells

The bound anti-TK1 antibodies are utilized to initiate complement mediated lysis destroying the virally infected cells. This embodiment is particularly effective because the anti-TK1 antibody binds specifically to virally infected cells expressing large amounts of TK1. Because the anti-TK1 antibody binds specifically to virally infected cells expressing large amount of TK1, it is targeted specifically to virally infected cells and thus the killing of these virally infected cells by complement mediated lysis is preferentially enhanced relative to the killing of normal cells. Additionally, anti-TK1 antibody is useful in many types of viral infection. Complement mediated lysis is a process well known in the art. The selection of an appropriate complement pathway is within the knowledge of one skilled in the art and could be accomplished without the expense of undue experimentation.

HIV infected lymphocytes are collected and assayed for complement mediated lysis. 2 mls of HIV infected lymphocytes are removed from a culture kept between $5 \times 10^5$ and $1 \times 10^6$ cells per ml from culture. The cells are centrifuged at 1600 rpm for 10 minutes. The supernatant is discarded and the cells are washed three times with PBS.

The hybridoma supernatant is diluted with PBS by a dilution factor of 1:2. The cells are incubated in diluted supernatant for one hour on ice.

After one hour, the cells are washed three times and resuspended in one ml of PBS. 3 mls of serum are added to the cells, and 3 mls of PBS is added to control cells. The cells are placed in a 37° water bath for one hour. The cells are removed from the waterbath and placed on a microscope slide for observation.

What is observed is that the lymphocytes from the uninfected population do not lyse in the presence or the absence of serum. However, the HIV infected lymphocytes lyse in the presence of serum, indicating the presence of the TK1 antigen. This demonstrates that treatment of HIV infection with anti-TK1 antibody can promote destruction of infected cells by complement mediated lysis.

Example 13

Utilizing Anti-TK to Target and Destroy Virally-Infected Cells

A variety of therapeutic applications are possible based on the knowledge that TK1 is found on the surface of virally-infected cells. For example, it is possible that an anti-cancer drug might selectively target and kill cells expressing TK1 on the cell surface. Thus, an anti-cancer drug is used to treat viral infection as well. This tactic is exemplified by cancer therapies that use Adenoviruses to infect cells with a plasmid that encodes a viral TK1gene, which then could be targeted to be killed by interrupting DNA synthesis. This embodiment is further exemplified by the therapeutic application of anti-TK1 antibodies, including anti-TK1 antibodies coupled with anti-tumor agents. An anti-tumor agent is coupled to the anti-TK antibody, which enhances the cytotoxic effects of the anti-TK1 antibody, and thus the killing of viral-infected cells relative to the killing of normal cells.

Example 14

Anti-TK1 Binding Active Sites of TK1 to Treat Viral Infection

Additionally, this invention contemplates using anti-TK1 antibodies for targeted therapy. For example, the anti-TK1 antibody is used to inhibit the elevated levels of TK1 and to restore a normal level of TK1, which helps reduce cellular replication. The anti-TK1 antibody may be used to inhibit the elevated level and to restore a normal level of TK1 enzyme activity in viral-infected cells, which decreases cellular proliferation and halts spread of the disease.

Example 15

Kits which Utilize Monoclonal Antibodies for Therapeutic Purposes

Further, the invention contemplates kits for performing the described methods. A kit for performing the above methods may comprise one or more monoclonal antibodies, for example, anti-TK1. In one embodiment, the monoclonal antibody would be conjugated with or packaged in conjunction with other agents, for example immunotoxins or commercially available complement, that when used would have therapeutic effects on the intended patients.

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A method for treating a viral infection in a mammal, said infection being characterized by increased expression of TK1 by virally-infected cells, said method comprising administering to said mammal an amount of a pharmaceutical composition comprising an anti-TK1 antibody, or fragment thereof, sufficient to inhibit viral replication or reduce viral burden in said mammal.

2. The method of claim 1, wherein said anti-TK1 antibody is a monoclonal antibody.

3. The method of claim 2, wherein said anti-TK1 monoclonal antibody is 5G11.

4. The method of claim 1, wherein said anti-TK1 antibody is a humanized or fully human monoclonal antibody.

5. The method of claim 1, wherein said pharmaceutical composition further comprises a second antiviral agent.

6. The method of claim 5, wherein said second antiviral agent is selected from the group consisting of nucleoside analogs, non-nucleoside analogs, protease inhibitors, and entry inhibitors.

7. The method of claim 1, wherein said anti-TK1 antibody is conjugated to a cytotoxic agent.

8. The method of claim 7, wherein said cytotoxic agent is selected from the group consisting of pokeweed antiviral protein (PAP), ricin, abrin, gelonin, saporin, and alpha-sarcin.

9. The method of claim 1, wherein prior to administering said pharmaceutical composition, said mammal is treated with sufficient radiation to up-regulate TK1 expression.

10. The method of claim 1, wherein said pharmaceutical composition further comprises a pharmaceutically acceptable liquid carrier adapted for parenteral administration.

11. The method of claim 10, wherein said liquid carrier comprises isotonic saline.

* * * * *